US010258931B2

(12) United States Patent
Hong et al.

(10) Patent No.: US 10,258,931 B2
(45) Date of Patent: Apr. 16, 2019

(54) POLYVINYLIDENE FLUORIDE HOLLOW FIBER MEMBRANE OF IN-SITU PORE-FORMING AGENT AND PREPARATION METHOD THEREFOR

(71) Applicant: UNITED ENVIRONTECH (XIAMEN) CO., LTD, Xiamen (CN)

(72) Inventors: Jianchun Hong, Xiamen (CN); Songhua Huang, Xiamen (CN); Xueping Ling, Xiamen (CN); Shiwei Wu, Xiamen (CN)

(73) Assignee: UNITED ENRIRONTECH (XIAMEN) CO., LTD., Xiamen (CN)

( * ) Notice: Subject to any disclaimer, the term of this patent is extended or adjusted under 35 U.S.C. 154(b) by 139 days.

(21) Appl. No.: 15/654,931

(22) Filed: Jul. 20, 2017

(65) Prior Publication Data

US 2017/0312699 A1   Nov. 2, 2017

Related U.S. Application Data

(63) Continuation of application No. PCT/CN2015/089138, filed on Sep. 8, 2015.

(30) Foreign Application Priority Data

Jan. 22, 2015 (CN) .......................... 2015 1 0031850

(51) Int. Cl.
*B01D 67/00* (2006.01)
*B01D 69/08* (2006.01)
(Continued)

(52) U.S. Cl.
CPC ........ *B01D 69/125* (2013.01); *B01D 67/0011* (2013.01); *B01D 69/08* (2013.01);
(Continued)

(58) Field of Classification Search
None
See application file for complete search history.

(56) References Cited

U.S. PATENT DOCUMENTS

| 5,782,983 A * | 7/1998 | Inada ..................... B01D 12/00 134/1 |
| 2009/0274944 A1 * | 11/2009 | Hasegawa .......... B01D 67/0083 429/481 |

FOREIGN PATENT DOCUMENTS

| CN | 101108314 A | 1/2008 |
| CN | 101590374 A | 12/2009 |

(Continued)

*Primary Examiner* — Krishnan S Menon
(74) *Attorney, Agent, or Firm* — Wayne & Ken, LLC; Tony Hom

(57) ABSTRACT

The present invention discloses a polyvinylidene fluoride hollow fiber membrane and a preparation method thereof. The hollow fiber membrane comprises 30%-50% of polyvinylidene fluoride resin, 40%-60% of inorganic molecular solution in-situ pore-forming agent and 5%-20% of organic diluent. The preparation method comprises preparing the inorganic molecular solution in-situ pore-forming agent formed from organic sol, mixing the inorganic molecular solution in-situ pore-forming agent formed from the organic sol with high-molecular polymer resin and the organic diluent to obtain a material A, extruding hollow fibers through a forming mold, stretching on line by 2-3 times to obtain hollow fiber filaments, extracting the hollow fiber filaments with an organic solvent to remove all organic matters, removing inorganic matters dispersed in the hollow fiber filaments by using an acid or alkaline solution to form a porous membrane and cleaning the porous membrane, setting and performing heat treatment to obtain the polyvinylidene fluoride hollow fiber membrane.

7 Claims, 2 Drawing Sheets

(51) Int. Cl.
*B01D 69/12* (2006.01)
*B01D 71/34* (2006.01)
*C07C 19/03* (2006.01)
*C08F 14/22* (2006.01)
*C08K 5/098* (2006.01)
*C08L 27/16* (2006.01)

(52) U.S. Cl.
CPC .............. *B01D 71/34* (2013.01); *C07C 19/03* (2013.01); *C08F 14/22* (2013.01); *C08K 5/098* (2013.01); *B01D 2323/18* (2013.01)

(56) References Cited

FOREIGN PATENT DOCUMENTS

| | | |
|---|---|---|
| CN | 201664580 U | 12/2010 |
| CN | 102179187 A | 9/2011 |
| CN | 101590374 B | 9/2012 |
| CN | 103409738 A | 11/2013 |
| CN | 103706259 A | 4/2014 |
| CN | 103877869 A | 6/2014 |
| CN | 103908898 A | 7/2014 |
| CN | 104524988 A | 4/2015 |
| EP | 0574957 A2 | 12/1993 |
| WO | 2013181297 A1 | 12/2013 |
| WO | 2014043315 A1 | 3/2014 |

\* cited by examiner

POLYVINYLIDENE FLUORIDE HOLLOW FIBER MEMBRANE OF IN-SITU PORE-FORMING AGENT AND PREPARATION METHOD THEREFOR

TECHNICAL FIELD

The present invention relates to a hollow fiber membrane, and more specifically, to a polyvinylidene fluoride hollow fiber membrane for an inorganic molecular solution in-situ pore-forming agent by utilizing organic sol and a preparation method thereof.

BACKGROUND OF THE INVENTION

A Membrane Bioreactor (MBR) organically combines a traditional biological wastewater treatment method and a modern membrane separation technology together, and is a treatment method for efficiently treating wastewater and improving water quality. A high-quality membrane material with a uniform synthetic pore size is a key problem in the MBR. Polyvinylidene Fluoride (PVDF) is an emerging membrane material with excellent comprehensive performance, has high mechanical strength, good resistance to acid and alkali and other severe environmental conditions and good chemical stability, has characteristics of high separation accuracy and high efficiency and has wide application prospects in the field of membrane separation. At present, preparation methods of a polyvinylidene fluoride hollow fiber membrane mainly comprise a solution phase inversion method and a thermally induced phase separation method. The hollow fiber membrane prepared by the solution phase inversion method has great water flux and high selectivity; the membrane prepared by the thermally induced phase separation method has advantages of porous structure and permeability controllability; and the two methods are widely applied in preparation of the membrane material. However, hollow fiber membrane filaments prepared by the solution phase inversion method have poor mechanical strength and are embrittled and degraded in chemical cleaning, particularly in soda-wash solution cleaning. The membrane filaments prepared by the thermally induced phase separation method with high mechanical strength is 4-5 times than that of the membrane filaments prepared by the solution phase inversion method with high chemical resistance. The mechanical strength of the membrane filaments is not changed in the chemical cleaning, particularly in the soda-wash solution cleaning. Therefore, the life of the hollow fiber membrane filaments prepared by the thermally induced phase separation method is longer than that of the hollow fiber membrane filaments prepared by the solution phase inversion method.

A membrane component in the MBR has higher requirements for pore size, water permeability, mechanical strength and chemical resistance of the membrane filaments particularly in industrial wastewater treatment, so the polyvinylidene fluoride hollow fiber membrane prepared by the thermally induced phase separation method is more applicable to the membrane component of the MBR and plays an important role in preparation of the membrane component of the MBR. How to prepare a controllable, uniform and well dispersive pore size is a key point and a difficulty in the preparation process of the membrane component.

In a Chinese patent with a publication number of CN201664580U, pore-forming agents and additives in an ultrafiltration membrane, a micro-filtration membrane and a reverse osmosis membrane arranged in a meshed centrifuging cylinder or wound outside a centrifugal winding cylinder are removed by adopting a centrifugal action produced by rotating the centrifuging cylinder, thereby achieving a purpose of removing and recycling the pore-forming agents and additives in the ultrafiltration membrane, the micro-filtration membrane and the reverse osmosis membrane. In a Chinese patent with a publication number of CN103706259A, a preparation method is as follows: a foamed pore-forming agent of sodium borohydride is introduced into a membrane forming system and reacts to produce uniformly distributed micro-bubbles so as to form a porous structure, so that a macroporous defect of the membrane is not formed while membrane porosity is improved. In a Chinese patent with a publication number of CN101108314A, a formula including hydrophilicity and other parameters is established, and the membrane is synthesized by a single membrane material PES in a casting solution formulation on the basis of comprehensive quantitative analysis by controlling the pore size mainly. A Chinese patent with a publication number of CN101590374B describes preparation of a high-strength hollow fiber membrane by a thermally induced phase separation method by using a formulation of polymer powder, a nanoscale inorganic pore-forming agent and an organic pore-forming agent.

Although the preparation of the membrane component is improved and innovated in the patents above, wastewater types are complicated and requirements for MBR membranes are relatively high. For example, in the Chinese patent with the publication number of CN101590374B, even if the nanoscale inorganic pore-forming agent is used, actually nano particles exist in an aggregation manner generally. Relative to high mixing of solids and solutions, high mixing of solids and solids is difficult to uniformly mix, so it is urgent to develop a hydrophobic molecular inorganic molecular solution pore-forming agent capable of realizing controllability, uniformity, good dispersity and good compatibility with a high-molecular polymer and to prepare the polyvinylidene fluoride hollow fiber membrane prepared by the thermally induced phase separation method.

SUMMARY OF THE INVENTION

The purpose of the present invention is to provide a polyvinylidene fluoride hollow fiber membrane for an inorganic molecular solution in-situ pore-forming agent formed by utilizing organic sol and a preparation method thereof with respect to the problems of above existing prepared membrane component, such as non-uniform in membrane filament pore size, low in dispersity, uncontrollable in the preparation process.

The polyvinylidene fluoride hollow fiber membrane for the in-situ pore-forming agent comprises the following raw materials in percentage by mass: 30%-50% of polyvinylidene fluoride resin;

40%-60% of inorganic molecular solution in-situ pore-forming agent formed from organic sol calculated by an amount of inorganic salts; and 5%-20% of organic diluents.

The polyvinylidene fluoride resin may adopt a homopolymer of polyvinylidene fluoride or a copolymer of polyvinylidene fluoride, and preferably adopts the homopolymer of polyvinylidene fluoride.

The inorganic molecular solution in-situ pore-forming agent formed from organic sol may adopt at least one of soluble acetate and nitrate, wherein one of zinc ion, zirconium ion, titanium ion, silicon ion, etc. is adopted as inorganic ion; zinc acetate, etc. is adopted as the acetate; and zinc nitrate, etc. is adopted as the nitrate. The inorganic molecular solution in-situ pore-forming agent formed from organic sol may adopt a stabilizer. The stabilizer may adopt an alcohol amine complexing agent, and the alcohol amine complexing agent is preferably ethanol amine. Organic solvents adopted in the inorganic molecular solution in-situ pore-forming agent formed from organic sol may adopt polyalcohol monoethers, polyalcohol polyethers or monoalcohol monoethers, and preferably adopts ethylene glycol monomethyl ether.

Vegetable oil or oleate may be adopted as the organic diluent; epoxidized soybean oil, etc. may be adopted as the vegetable oil; at least one of ethyl oleate, glyceryl monooleate, oleoyl macrogolglycerides, etc. may be adopted as the oleate; and the organic diluent is preferably the epoxidized soybean oil or oleoyl macrogolglyceride.

In the formulation above, a proper amount of assistants can be added according to needs, such as antioxidants, lubricating agents, heat stabilizers, ultraviolet light absorbers and other hydrophilic additives.

A preparation method for the polyvinylidene fluoride hollow fiber membrane for the in-situ pore-forming agent comprises the following steps:

a. preparing an inorganic molecular solution in-situ pore-forming agent formed from organic sol;

b. mixing the inorganic molecular solution in-situ pore-forming agent formed from organic sol with high-molecular polymer resin and the organic diluent to obtain a material A;

c. extruding the material A to obtain hollow fibers through a forming mold;

d. stretching the hollow fibers on line by 2-3 times to obtain hollow fiber filaments;

e. extracting the stretched hollow fiber filaments with an organic solvent to remove all organic matters, and removing inorganic matters dispersed in the hollow fiber filaments by using an acid or alkaline solution to form a porous membrane; and f. cleaning the porous membrane, setting and performing heat treatment to obtain the polyvinylidene fluoride hollow fiber membrane for the in-situ pore-forming agent.

In the step a, a specific preparation method for the inorganic molecular solution in-situ pore-forming agent formed from organic sol can comprise the steps: dissolving a soluble inorganic salt of zinc such as zinc nitrate (Zn(NO3)2 or an organic salt of zinc such as zinc acetate (Zn(CH3COO)2) and the like in ethylene glycol monomethyl ether and other organic solvents to form a solution in the presence of a catalyst of glacial acetic acid and a stabilizer of ethanol amine; dissolving the zinc acetate in the ethylene glycol monomethyl ether; adding ethanol amine with an equal molar ratio to the zinc acetate; fully stirring at a temperature of 40° C.-80° C. (preferably 50° C.-70° C.) for 1-2 hours; and forming a transparent, homogeneous and stable complexing solution, i.e., the inorganic molecular solution in-situ pore-forming agent formed from organic sol; and a reaction equation is as follows:

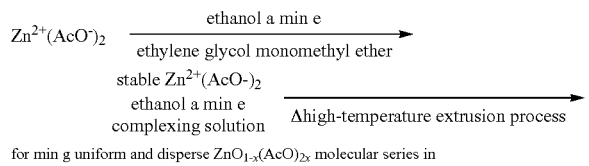

In the step b, a specific method for mixing the inorganic molecular solution in-situ pore-forming agent formed from organic sol with the high-molecular polymer resin and the organic diluent can comprise the steps: mixing the polyvinylidene fluoride resin (30%-50%), the inorganic molecular solution in-situ pore-forming agent formed from organic sol (40%-50%, calculated by the amount of inorganic salts) and the organic diluents (10%-20%) in a high-speed mixing agitator to form a uniform material, i.e., uniformly mixing the inorganic molecular solution in-situ pore-forming agent formed from organic sol and the organic diluent with the solid high-molecular polymer resin.

In the step c, the extrusion can be performed by a molding machine.

The step d of stretching the hollow fibers on line is to perform uniaxial stretching according to 50%-100% along a longitudinal direction of the hollow fiber filaments by utilizing rollers of different peripheral speeds and wind the hollow fiber filaments on a filament take-up wheel.

In the step e, an organic solvent extraction agent can be adopted during organic solvent extraction treatment and selected from chlorinated hydrocarbon or alcohol of low molecular weight, and preferably from the chlorinated hydrocarbon, and dichloromethane and the like can be adopted as the chlorinated hydrocarbon.

Hydrochloric acid or sulfuric acid and the like may be adopted as the acid, the sodium hydroxide or potassium hydroxide and the like may be adopted as alkali, and preferably a strong acid or strong base removing agent of the organic matters and the inorganic matters is hydrochloric acid and sulfuric acid solution.

In the step f, the cleaning can be performed with water, and a heat treatment temperature may be 120° C.-140° C.

Compared with the prior art, the inorganic molecular solution formed from organic sol in the present invention, that is, the stable molecular complexing solution, has excellent compatibility with the high-molecular polymer, high dispersity and uniformity, and the prepared hollow fiber membrane remains original due characteristics of membrane filaments prepared by a thermally induced phase separation process and further has a uniform meshed structure in a three-dimensional space, so that distribution of membrane pores is more uniform. The hollow fiber membrane is applicable to multiple wastewater treatment MBRs.

DETAILED DESCRIPTION OF THE INVENTION

The present invention is further described below in combination with drawings through embodiments.

A ratio of each raw material is mass percentage if not defined.

Embodiment 1

Figure 1:
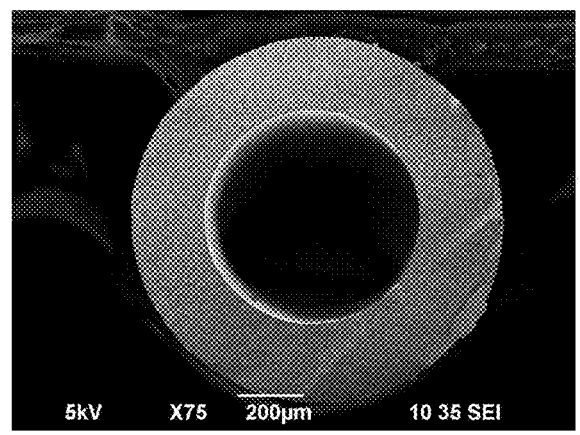
FIG. 1 is a section scanning electron-microscope photo of a polyvinylidene fluoride hollow fiber membrane for an inorganic molecular solution in-situ pore-forming agent formed by utilizing organic sol prepared in embodiments.
Figure 2:
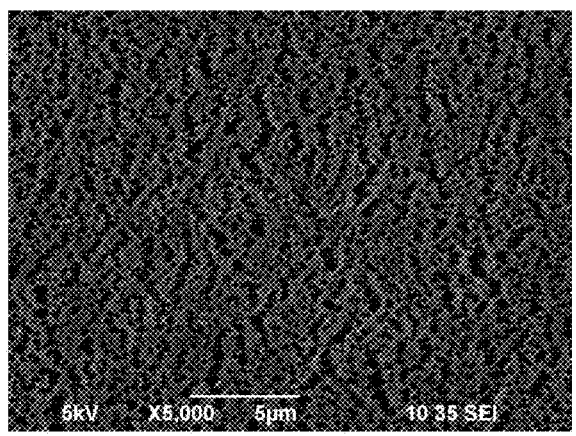
FIG. 2 is an outer surface scanning electron-microscope photo of a polyvinylidene fluoride hollow fiber membrane for an inorganic molecular solution in-situ pore-forming agent formed by utilizing organic sol prepared in embodiments.

The preparation method comprises the following steps:
1) dissolving a certain amount of zinc acetate in ethylene glycol monomethyl ether in an in-situ pore-forming agent, adding an ethanol amine solution with an equal molar ratio to the zinc acetate, stirring at a temperature of 65° C. under catalysis of a little glacial acetic acid, and finally preparing a homogeneous and transparent solution with a zinc ion concentration of 10%-30%; and
2) mixing 40% of a polyvinylidene fluoride resin PVDF, 6.5% of oleoyl macrogolglyceride, 3.5% of epoxidized soybean oil and 50% of a zinc molecular solution in-situ pore-forming agent formed by organic sol prepared in the step 1) in a high-speed mixer at high speed, uniformly dispersing polyvinylidene fluoride resin solids in a uniform organic phase, performing 170 mixing by using a screw extruder, extruding hollow fiber filaments by a hollow fiber mold, solidifying with cooling water in a cooling tank, performing uniaxial stretching by 80%, and winding the hollow fiber filaments on a filament take-up wheel; discharging the hollow fiber filaments from the wheel, then soaking with dichloromethane twice at a room temperature for 1 hour to remove all organic matters, soaking once in 10% of sulfuric acid solution for 30 minutes to remove all inorganic matters, and finally repeatedly flushing with pure water, airing and performing heat setting in a drying oven at a temperature of 140° C. for 3 hours to obtain the final product. Performance test data of hollow fiber membrane samples is shown in Table 1, and sections and outer surfaces of the membrane filaments are shown in FIG. 1 and FIG. 2.

Embodiment 2

1) A preparation method of an in-situ pore-forming agent adopts the same formulation as that in the step 1) of embodiment 1.
2) Processes of preparing the hollow fiber membrane are the same as those in embodiment 1, while the difference is that: 50% of polyvinylidene fluoride resin, 6.5% of oleoyl macrogolglyceride, 3.5% of epoxidized soybean oil and 40% of zinc molecular solution in-situ pore-forming agent formed by organic sol prepared in the step 1) are mixed to obtain the final product. Performance test data of hollow fiber membrane samples is shown in Table 1.

TABLE 1

| | | | Membrane sample performance parameters | | | | | |
|---|---|---|---|---|---|---|---|---|
| Embodiments | Outer diameter (mm) | Inner diameter (mm) | Membrane pore size (μm) | Porosity (%) | Flux (L/m2*h) | Tensile strength at break (MPa) | Tensile elongnation at break | Compressive strength (MPa) |
| 1 | 1.25 | 0.62 | 0.1 | 70 | 1350 | 8.5 | 85 | >1 |
| 2 | 1.21 | 0.58 | 0.06 | 63 | 780 | 9.7 | 90 | >1 |

The inorganic molecular solution formed from organic sol in the present invention, that is, the stable molecular complexing solution, has excellent compatibility with the high-molecular polymer, high dispersity and uniformity. The prepared hollow fiber membrane remains original due characteristics of membrane filaments prepared by the thermally induced phase separation process and further has a uniform meshed structure in a three-dimensional space, so that distribution of membrane pores is more uniform. The hollow fiber membrane is applicable to multiple wastewater treatment MBRs.

What is claimed is:
1. A preparation method for a polyvinylidene fluoride hollow fiber membrane comprising the following raw materials in percentage by mass:
30%-50% of polyvinylidene fluoride resin;
40%-60% of inorganic molecular solution in-situ pore-forming agent formed from organic sol calculated by mass of zinc acetate; and
5%-20% of organic diluent;
wherein the polyvinylidene fluoride resin is a homopolymer of polyvinylidene fluoride or a copolymer of polyvinylidene fluoride;
wherein the inorganic molecular solution in-situ pore-forming agent formed from organic sol adopts zinc acetate; organic solvents in the inorganic molecular solution in-situ pore-forming agent formed from organic sol are polyalcohol monoethers, polyalcohol polyethers or mono-alcohol monoethers;
wherein the inorganic molecular solution in-situ pore-forming agent formed from organic sol is prepared by the following method: dissolving the zinc acetate in an organic solvent of ethylene glycol monomethyl ether to form a solution in the presence of a catalyst of glacial acetic acid and a stabilizer of ethanol amine, wherein the added ethanol amine and zinc acetate have an equal molar ratio; stirring at a temperature of 40-80° C. for 1-2 hours to form a transparent, homogeneous and stable complexing solution, and obtaining the inorganic molecular solution in-situ pore-forming agent formed from organic sol;
the method comprising the following steps:
a. preparing an inorganic molecular solution in-situ pore-forming agent formed from organic sol;
b. mixing the inorganic molecular solution in-situ pore-forming agent formed from organic sol with high-molecular polymer resin and an organic diluent to obtain a material A;
c. extruding the material A to obtain hollow fibers through a forming mold;
d. stretching the hollow fibers on line by 2-3 times to obtain hollow fiber filaments;
e. extracting the stretched hollow fiber filaments with an organic solvent to remove all organic matters, and removing inorganic matters dispersed in the hollow fiber filaments by using an acid or alkaline solution to form a porous membrane; and
f. cleaning the porous membrane, setting and performing heat treatment to obtain the polyvinylidene fluoride hollow fiber membrane for the in-situ pore-forming agent.

2. The preparation method for the polyvinylidene fluoride hollow fiber membrane according to claim 1, wherein in the step c, the extrusion is performed by a molding machine; and
the step d of stretching the hollow fibers on line is to perform uniaxial stretching according to 50%-100% along a longitudinal direction of the hollow fiber filaments by utilizing rollers of different peripheral speeds and wind the hollow fiber filaments on a filament take-up wheel.

3. The preparation method for the polyvinylidene fluoride hollow fiber membrane according to claim 1, wherein in the step e, the organic solvent extraction treatment is performed by an organic solvent extraction agent and the organic solvent extraction agent is selected from chlorinated hydrocarbon or alcohol of low molecular weight.

4. The preparation method for the polyvinylidene fluoride hollow fiber membrane according to claim 3, wherein the the organic solvent extraction agent is chlorinated hydrocarbon.

5. The preparation method for the polyvinylidene fluoride hollow fiber membrane according to claim 4, wherein the chlorinated hydrocarbon is dichloromethane.

6. The preparation method for the polyvinylidene fluoride hollow fiber membrane according to claim 1, wherein the acid is hydrochloric acid or sulfuric acid, and the alkali is sodium hydroxide or potassium hydroxide.

7. The preparation method for the polyvinylidene fluoride hollow fiber membrane according to claim 1, wherein in the step f, the cleaning is performed with water, and a heat treatment temperature is 120° C.-140° C.

\* \* \* \* \*